(12) United States Patent
Graser et al.

(10) Patent No.: US 11,209,368 B2
(45) Date of Patent: Dec. 28, 2021

(54) METHOD FOR DETECTING SPECIFIC NUCLEIC ACID SEQUENCES

(71) Applicant: IST Innuscreen GmbH, Berlin (DE)

(72) Inventors: Elmara Graser, Berlin (DE); Timo Hillebrand, Hoppegarten (DE)

(73) Assignee: IST Innuscreen GmbH, Berlin (DE)

( * ) Notice: Subject to any disclaimer, the term of this patent is extended or adjusted under 35 U.S.C. 154(b) by 219 days.

(21) Appl. No.: 16/043,109

(22) Filed: Jul. 23, 2018

(65) Prior Publication Data

US 2018/0356345 A1 Dec. 13, 2018

Related U.S. Application Data

(63) Continuation of application No. 13/639,774, filed as application No. PCT/EP2011/055515 on Apr. 8, 2011, now abandoned.

(30) Foreign Application Priority Data

Apr. 8, 2010 (DE) .................. 10 2010 003 781.8

(51) Int. Cl.
*C12P 19/34* (2006.01)
*G01N 21/64* (2006.01)
*C12Q 1/6818* (2018.01)
*C12Q 1/686* (2018.01)

(52) U.S. Cl.
CPC ......... *G01N 21/6486* (2013.01); *C12Q 1/686* (2013.01); *C12Q 1/6818* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| 5,210,015 A | 5/1993 | Gelfand et al. |
| 5,487,972 A | 1/1996 | Gelfand et al. |
| (Continued) | | |

FOREIGN PATENT DOCUMENTS

| DE | 198 11 731 | 9/1999 |
| DE | 102 50 946 | 5/2004 |
| (Continued) | | |

OTHER PUBLICATIONS

TaqMan from Wikipedia. Printed on Aug. 7, 2020.*
(Continued)

*Primary Examiner* — Frank W Lu
(74) *Attorney, Agent, or Firm* — Grüneberg and Myers PLLC

(57) ABSTRACT

A method and test kit are useful for detecting specific nucleic acid sequences. The process includes (1) matrix-dependent new synthesis of the target nucleic acid; (2) target-specific probe hybridization; and (3) detection of the hybridization event. In the first step, an oligonucleotide 1, which is marked by a marker 1 and is entirely or partially complementary to the target sequence, acts as a primer in the matrix-dependent new synthesis of the target nucleic acid and, in the second step, an oligonucleotide 2, which is marked by a marker 2 and, owing to its melting temperature being lower than that of the oligonucleotide 1, is not involved in the first step, partially or completely hybridizes with the DNA new synthesis product of oligonucleotide 1.

9 Claims, 6 Drawing Sheets

Specification includes a Sequence Listing.

(56) References Cited

U.S. PATENT DOCUMENTS

| | | | |
|---|---|---|---|
| 5,573,906 | A | 11/1996 | Bannwarth et al. |
| 5,914,230 | A | 6/1999 | Liu et al. |
| 6,174,670 | B1 | 1/2001 | Wittwer et al. |
| 6,403,339 | B1 | 6/2002 | Bertling |
| 10,287,636 | B2* | 5/2019 | Hillebrand ............. C12Q 1/689 |
| 2002/0177127 | A1 | 11/2002 | Yang et al. |
| 2003/0087239 | A1 | 5/2003 | Stanton et al. |
| 2005/0171222 | A1 | 8/2005 | Tanaka et al. |
| 2007/0026423 | A1 | 2/2007 | Koehler et al. |
| 2010/0099099 | A1 | 4/2010 | Graser et al. |
| 2010/0184036 | A1 | 7/2010 | Fu |
| 2010/0221718 | A1 | 9/2010 | Hillebrand et al. |
| 2011/0212846 | A1 | 9/2011 | Spier |
| 2011/0257018 | A1* | 10/2011 | Larsen ................. C12Q 1/6869 506/2 |
| 2013/0115597 | A1 | 5/2013 | Graser et al. |
| 2015/0024386 | A1 | 1/2015 | Hillebrand et al. |

FOREIGN PATENT DOCUMENTS

| | | |
|---|---|---|
| DE | 10 2005 000 021 | 9/2006 |
| EP | 0 566 751 | 10/1993 |
| EP | 0 972 848 | 1/2000 |
| EP | 0 826 066 | 9/2000 |
| EP | 1 384 789 | 1/2004 |
| JP | 2001-29072 | 2/2001 |
| KR | 10 2006 099022 | 9/2006 |
| WO | 2003/051967 | 6/2003 |
| WO | 2003/072051 | 9/2003 |
| WO | 2005/051967 | 6/2005 |
| WO | 2006/041524 | 4/2006 |
| WO | 2008/104791 | 9/2008 |
| WO | 2009/000764 | 12/2008 |
| WO | 2009/126678 | 10/2009 |

OTHER PUBLICATIONS

Written Opinion of the International Searching Authority dated Jul. 7, 2011 in PCT/EP2011/055515, with English translation.

International Preliminary Report on Patentability dated Oct. 9, 2012 in PCT/EP2011/055515.

Bernard et al., "Integrated Amplification and Defection of the C677T Point Mutation in the Methylenetetrahydmfolate Reductase Gene by Fluorescence Resonance Energy Transfer and Probe Melting Curves," Analytical Biochemstry, 255. pp 101-107, 1998.

Lyon et al., "LightCycler Technology in Molecular Diagnostics," Journal of Molecular Diagnostics, vol. 11, No. 2, pp. 93-101, 2009.

Piepenburg et al., "DNA Detection Using Recombination Proteins," PLOS Biology, vol. 4, issue 7, pp. 1115-1121, Jul. 2006.

International Search Report dated Jul. 7, 2011 in PCT/EP2011/55515 with English-language translation.

U.S. Appl. No. 12/644,982, filed Dec. 22, 2009, 2010/0221718, Hillebrand et al.

U.S. Appl. No. 12/559,252, filed Sep. 14, 2009, 2010/0099099, Graser et al.

U.S. Appl. No. 13/639,774, filed Jan. 15, 2013, 2013/0115597, Graser et al.

U.S. Appl. No. 14/299,674, filed Jun. 9, 2014, 2015/0024386, Hillebrand et al.

Aptima HCV RNA Qualitative Assay protocol from Gen-Probe Incorporated. 2006-2011 Gen-Probe Incorporated. Revised on Nov. 2011.

Nucleotide sequence comparison between Rickettsia antisense primer and Rickettsia raoultii clone HL02 citrate synthase (gltA) gene, printed on Dec. 26, 2014.

Nucleotide sequence comparison between Rickettsia hybridization probe and Rickettsia raoultii clone HL02 citrate synthase (gltA) gene, printed on Dec. 26, 2014.

Nucleotide sequence comparison between SEQ ID No. 15 from Bannwarth et al., and gag protein gene of HIV-1 isolate GAG_Chronic_39 USA, printed on Dec. 27, 2014.

Oligos Melting Temperature from Sigma-Aldrich, printed on Dec. 26, 2014.

Sequence comparison between Listeria monocytogenes probe (SEQ ID No. 3) and complete genome of Listeria monocytogenes strain PNUSAL000096, printed on Jun. 20, 2017.

* cited by examiner

|   | 1 | 2 | 3 | 4 | 5 | 6 | 7 | 8 | 9 | 10 | 11 | 12 |
|---|---|---|---|---|---|---|---|---|---|----|----|----|
| A | 868.4 | 233.4 | 691.1 | 1482.6 | 984.6 | 716.6 | 1151.5 | 1120.8 | 708.7 | 1092.3 | 1228.0 | 885.9 |
| B | -597.9 | 482.2 | 3447.3 | 6533.3 | 6024.7 | 18408.0 | 11764.7 | 18937.0 | 11258.9 | 26666.0 | 18937.8 | 860.0 |
| C | -2205.8 | -621.4 | 251.0 | -3036.2 | 187.8 | -729.9 | 1032.3 | -2284.8 | -1892.6 | -218.2 | -2041.2 | -2173.0 |

Fig. 2

|   | 1 | 2 | 3 | 4 | 5 | 6 | 7 | 8 | 9 | 10 | 11 | 12 |
|---|---|---|---|---|---|---|---|---|---|---|---|---|
| A | -2599.2 | -3259.9 | -3929.1 | -2749.5 | -1874.1 | 127.4 | 5371.4 | -578.7 | -2628.2 | -921.3 | -2710.9 | -1993.3 |
| B | -4639.8 | -4207.2 | 6152.9 | 1889.3 | 6473.8 | 9503.8 | 10678.1 | -3283.8 | 12896.6 | 14356.3 | -4802.5 | -1784.3 |
| C | -1507.6 | -1144.2 | 8942.4 | 5411.2 | 12327.0 | 12130.3 | 10502.1 | -988.1 | 15575.7 | 16529.2 | -249.9 | -1986.2 |
| D | -2007.7 | -641.9 | -5940.6 | -3160.5 | -4337.8 | -4988.4 | -3652.1 | -734.4 | -2680.5 | -1107.4 | -3966.0 | 1698.6 |

Fig. 4

METHOD FOR DETECTING SPECIFIC NUCLEIC ACID SEQUENCES

CROSS REFERENCE TO RELATED APPLICATIONS

The present application is a continuation of U.S. patent application Ser. No. 13/639,774, filed Oct. 5, 2012, incorporated herewith by reference, which is a 35 U.S.C. § 371 national stage patent application of International patent application PCT/EP2011/055515, filed on Apr. 8, 2011, published as WO/2011/124684 on Oct. 13, 2011, the text of which is incorporated by reference, and claims the benefit of the filing date of German application no. 10 2010 003 781.8, filed on Apr. 8, 2010, the text of which is also incorporated by reference.

FIELD OF THE INVENTION

The present invention relates to a method and a test kit for detecting specific nucleic acid sequences, comprising the steps of 1. matrix-dependent de novo synthesis of the target nucleic acid, 2. target-specific probe hybridization and 3. detection of the hybridization event. In this context the detection of the hybridization reaction may be accomplished both fluorimetrically in the form of a homogeneous assay and thereafter immunologically for verification of the result. The detection reaction always takes place chronologically after the matrix-dependent de novo synthesis has ended.

DISCUSSION OF THE BACKGROUND

Gene diagnostics have become an indispensable part of modern medical laboratory diagnostics, forensic diagnostics, veterinary medical laboratory diagnostics or food and environmental diagnostics.

Genetic diagnostics were revolutionized with the invention of the PCR technology, which makes it possible to amplify any desired nucleic acid sequence specifically.

Using PCR, there exists a large number of methods which, in combination with the PCR technology, also permit the specific detection of a completed amplification. In particular, to meet the requirements of exact genetic diagnostics, there must be used techniques that ensure that a generated amplification product also corresponds to the target sequence to be specifically detected. The widespread use of visualization of a PCR product by means of gel electrophoresis is not sufficient for this purpose.

One option for detecting specific nucleic acids that in principle is very rapid and can be accomplished without great experimental time and effort is known as the real-time PCR method. In this case the amplification reaction is coupled directly with the actual detection reaction.

A widely used method for detecting specific nucleic acids is the LightCycler technology of Roche. For this purpose the Roche Company developed special hybridization probes, consisting of two different oligonucleotides, each of which is labeled with only one fluorophore. The acceptor is located at the 3'-end of the one probe, while the other oligonucleotide has a donor at the 5'-end. The probes are chosen such that they both bind to the same DNA strand, wherein the distance between acceptor and donor is permitted to be only 1 to 5 nucleotides at most, so that the so-called FRET effect can develop. The fluorescence is measured during the annealing step, in which light of this wavelength is detectable only as long as both probes are bound to the DNA. In this system the melting points of both probes should be identical. By virtue of the use of two hybridizing probes in addition to the primers used, the specificity of this detection system is extremely high.

A further real-time PCR application for detection of specific nucleic acid targets can be performed with so-called double-dye probes, which were disclosed in U.S. Pat. Nos. 5,210,015 and 5,487,972 (TaqMan probes). Double-dye probes carry two fluorophores on one probe. In this case the reporter dye is located at the 5'-end and the quencher dye at the 3'-end. In addition, a phosphate group may also be located at the 3'-end of the probe, so that the probe cannot function as a primer during elongation. As long as the probe is intact, the released light intensity is low, since almost the entire light energy produced after excitation of the reporter is absorbed and converted due to the spatial proximity of the quencher. The emitted light of the reporter dye is "quenched", i.e. extinguished. This FRET effect continues to exist after the probe has bound to the complementary DNA strand. During the elongation phase, the polymerase encounters the probe and hydrolyzes it. The ability of the polymerase to hydrolyze an oligonucleotide (or a probe) during strand synthesis is known as 5'-3' exonuclease activity. Not all polymerases have 5'-3' exonuclease activity (Taq and Tth polymerase). This principle was described for the first time for Taq polymerase. The principle is known as the TaqMan principle. After probe hydrolysis, the reporter dye is no longer in the spatial proximity of the quencher. The emitted fluorescence is now no longer converted and this fluorescence increase is measured.

Further methods based on the FRET effect are also known, which methods detect both the decrease and the increase of the sample fluorescence.

In the publication JP 002001029072 AA, reporter and quencher are coupled on the individual dNTPs (deoxyribonucleotides) added to the reaction. When these nucleotides are incorporated into the amplified nucleic acid, the fluorescence of the sample is reduced by the FRET effect. A disadvantage of the method is the incorporation of the labeled nucleotides even in the case of mispriming and of primer dimers. Thus such a method cannot be used for diagnostic applications.

Further publications relate to methods in which the FRET pair labels are not attached to one oligonucleotide but instead are distributed over several primer or probe molecules.

In unexamined application WO 2009/126678 A2, two hybridization probes form a hairpin formation, by which the reporter and quencher approach one another spatially.

In unexamined application DE 10250948 A1, the respectively labeled probes are hybridized with one another. When a target nucleic acid is present, one of the probes is able to form a duplex with the target nucleic acid, whereby the FRET interaction is canceled.

In unexamined application DE 102005000021 A1, two labeled probes form a triplex with the target nucleic acid, wherein the fluorescence is released by the exonuclease activity of the Taq polymerase.

In the patent EP 1384789 B1 and in a publication cited in the patent (Bernard, P. S., at al. Anal Biochem 255 (1998) 101-7), one labeled primer and one labeled probe respectively are used for real-time observation of the amplification.

A further option for specific detection of amplification products by means of real-time PCR technology consists in the use of intercalating dyes (ethidium bromide, Hoechst 33258, Yo-Pro-1 or SYBR Green™, etc.). After excitation by high-energy UV light, these dyes emit light in the visible lower-energy wavelength range (fluorescence). If the dye is present as a free dye in the reaction mixture, the emission is very weak. It is only by the intercalation of the dye, i.e. by incorporation into the small furrows of double-strand DNA molecules, that the light emission is greatly intensified. The dyes are inexpensive and universally usable, since in principle any PCR reaction can be followed in real time with them. Moreover, they have a high signal strength, since every DNA molecule is able to bind several dye molecules. Nevertheless, an extreme disadvantage for application also results from the advantages: In principle, it is not possible with intercalating dyes to distinguish between correct product and amplification artifacts (such as primer dimers or nonconforming products). Formed primer dimers and other artifacts naturally also bind intercalating dyes and therefore lead to an unspecific increase of fluorescence even in negative samples. However, a clear differentiation between a specific amplification event and an artifact is absolutely necessary. In order to achieve this in any case, there is used a so-called melting-point analysis at the end of the actual PCR reaction. For this purpose the reaction mixture is heated in steps of 1 degree from 50° C. to 95° C. During this process the fluorescence is measured continuously. The point at which the double-strand DNA melts is characterized by a drop (peak) of the fluorescence of the intercalating dye, since the intercalating dye dissociates from the single-strand DNA. When the PCR is optimally adjusted, a sharply accentuated melting-point peak should be expected. This melting point represents the specific product to be expected. Products of different sizes and products from different sequences have different melting points.

Furthermore, by means of real-time PCR applications it is also possible to achieve quantification of the target to be detected.

As already explained, the described methods satisfy the requirement of specific detection of an amplification product.

Nevertheless, a major disadvantage exists in the fact that they are implemented on very expensive instrumental platforms, which must combine the processes of both amplification and of subsequent optical detection appropriate for the problem in one hardware solution. Furthermore, many of these described detection methods are still based on real-time tracking of the amplification process. On the basis of this strategy, the processing of the measured fluorescence values also takes place in the course of the amplification reaction. It is clear to the person skilled in the art that an enormously high level of analysis algorithms must therefore be integrated into real-time systems. This ultimately explains the large financial expense that must be invested for the use of real-time PCR systems. Finally, even the operation of such instrumental systems necessitates a high level of expertise.

Besides the described diagnostic detection methods based on real-time PCR, however, alternative variants also exist for specific detection of nucleic acids.

In this connection, less expensive methods for detecting nucleic acids include, for example, PCR ELISA. In this method the DNA sequence to be investigated is amplified and the produced DNA fragment is then covalently immobilized on a solid phase (e.g. microtiter plate or strip), subsequently denatured to a single strand and hybridized with a sequence-specific probe. The successful binding of the probe can be visualized by an antibody-mediated color reaction. Another variant is based on immobilizing the probe on a solid phase and then bringing the PCR product after the end of denaturing into contact with the immobilized probe. The detection of a completed hybridization event takes place by analogy with the first method variant.

In principle, PCR ELISA techniques are simple to perform, but nevertheless comprise multiple process steps, so that several hours of working time to perform the subsequent detection method are also needed in addition to the time needed to perform the PCR. Such a method usually needs 8 hours and therefore is also not suitable as a rapid test.

Furthermore, some instruments such as a temperature-regulating station, a so-called washer or even a measuring instrument for detection of the hybridization signal are also necessary. In addition, further special instruments or special consumables may be necessary.

Further simple methods for detection of amplification products are based on amplification of the target sequences and subsequent hybridization of amplification products on a membrane. Even in these methods, several variants known to the person skilled in the art exist. Once again, however, these methods are laborious to perform, need a large number of process steps to be executed and are therefore not suitable as rapid tests. This then includes even the use of biochip strategies, which utilize the hybridization of PCR products with hybridization probes to detect the specificity. These methods are also complex and dependent on very expensive instrumental platforms.

A significant reduction of working steps is disclosed in the publication KR 1020060099022 A (Method and kit for rapid and accurate detection and analysis of nucleotide sequence with naked eye by using membrane lateral flow analysis).

In this case a so-called lateral-flow method is used to detect nucleic acids. This method also depends on the technology of hybridization of nucleic acids on a solid phase. One advantage of lateral flow methods is that they represent a small, manual test format (strip test).

A very rapid detection method that also depends on the detection of amplification products by means of a test strip and is commercially available is in turn based on a completely different principle from that in the above publication. In this case, the PCR reaction is performed with one biotinylated primer and one non-biotinylated primer. After completion of the PCR, a PCR product labeled with biotin at one end is therefore obtained. A test strip (e.g. of Millenia, Amodia, etc.) containing two separate binding sites is used for detection: a streptavidin site for coupling the biotin-labeled DNA strand and an FITC binding site for checking the function of the test strip.

The PCR product is detected by denaturing the PCR batch at the end of the PCR and hybridizing with a probe complementary to the biotin-labeled DNA strand. The probe is FITC-labeled.

For detection, the PCR hybridization batch is mixed with a run buffer and applied on the test strip. According to the description of the test, the biotinylated DNA strand binds to the streptavidin binding site of the strip. Detection is accomplished via the FITC label of the probe hybridized with the DNA strand. A typical signal in the form of a stripe appears. This signal is supposedly the specific detection of the amplification product. However, the method does not combine the hybridization of the probe with the PCR process but instead performs it as a separate method step.

Unexamined application WO 2009/000764 A2 permits the performance of amplification and hybridization of the PCR product in one reaction batch. In this case there is formed a doubly labeled amplificate-probe dimer, which can then be visualized, e.g. by means of a lateral-flow strip. This is a very inexpensive way of visualizing a PCR hybridization product, and in particular is independent of instrumentation. A disadvantage of this method, however, is that primarily it is not a homogeneous assay, since the reaction vessel must be opened after the amplification/hybridization reaction has taken place, in order that the amplification mixture can be transferred to a lateral-flow strip.

Thus the actual detection reaction takes place outside the reaction cavity in which the amplification/hybridization reaction is performed.

Also, the method does not permit any numerical display of the detection result, but is always limited merely to a YES-NO decision based on visual observation. Quantification of the reaction products is also not possible on a lateral-flow strip, since the upper limit is dictated by the binding capacity of the strip.

In International Patent Application WO 2005/51967 A2, labeled oligonucleotides with several fluorophores are described. The method for separating the fluorophores, including cleaving the labeled oligonucleotides, uses enzymes with 5'-exonuclease activity.

The subject matter of the publication WO 03/072051 A2 is a fluorescence energy transfer (FET) labeled probe with a nucleic acid intercalator, which contains a polycyclic compound bound to an FET-labeled oligonucleotide, wherein the nucleic acid intercalator is covalently bound at the 3'-end of the FET-labeled oligonucleotide, and wherein the FET-labeled oligonucleotide represents a dark quencher, which is positioned at its 3'-end, and wherein the FET-labeled probe is resistant to 3'-5'-exonuclease.

The publication of E Lyon et al., "LightCycler Technology in Molecular Diagnostics", J. Mol. Diagn (2009) 11 (2) 93-101, reports on a PCR with real-time fluorescence monitoring and melting curve analysis. This permits the PCR to be performed within 15 minutes. The review describes the significant advances of LightCycler technology within the last 15 years.

The objective of the present invention is to provide a universally usable method for specific detection of target nucleic acids, which method also makes it possible to perform the detection reaction in the form of a homogeneous assay, meaning that the detection of the detection reaction already takes place in the reaction cavity, in which the actual amplification/hybridization reaction is also occurring. Another objective was to permit diagnostic certainty of a detection reaction by quasi dual detection, since a series of test procedures necessitates not only a first detection reaction (such as real-time PCR) but also a second control detection (such as application of the amplification products on an agarose gel). As an expansion of the objective, such a novel method could also be used in such a way that the detection reaction takes place as a homogeneous assay (instrument-dependent) or else, as an alternative thereto, even as a test based on a lateral-flow strip (instrument-independent).

A method with a similar objective was published by Piepenburg et al. (PLOS biology, July 2006, Volume 4, Issue 7, 1115-1121). In this case a recombinase-coupled isothermal PCR is performed. The double-labeled probe has an integrated cut site for a nuclease. During hybridization of the probe, the formed double strand is cut by the nuclease and thereby the fluorescence is released. After having been cut with the nuclease, the labeled probe is able to function as a primer. Together with the other labeled primer, there is then formed a double-labeled PCR product, which can be detected on a LFA strip. One disadvantage is that this method is chemically very complex and difficult. Furthermore, even before the beginning of the test procedure, it must be decided which of the detection methods and therefore which labels are preferred. If such a decision were not made, then the probe must be prepared at a minimum of four sites: 1. reporter fluorophore, 2. quencher, 3. cut site of the nuclease, 4. amplification blockade at the 3'-end.

SUMMARY OF THE INVENTION

The present object was solved surprisingly simply according to the features of the Embodiments. The inventive method combines a matrix-dependent DNA de novo synthesis with a hybridization step. The inventive choice of labels of the oligonucleotides participating in the reactions permits not only a reaction-dependent fluorescence measurement and associated therewith a numerical and possibly quantitative evaluation but also instrument-independent visualization of the reaction, e.g. on a lateral-flow strip. It is also particularly advantageous that the detection of the fluorescence reduction following a FRET effect is possible with the inventive method in the form of end-point detection. From the instrumental viewpoint, such a measurement principle can therefore also dispense with the use of expensive real-time instrumental systems.

EMBODIMENTS

1. A method for detecting specific nucleic acid sequences (target), with the following steps:
   a) matrix-dependent DNA de novo synthesis of the target nucleic acid,
   b) target-specific probe hybridization and
   c) detection of the hybridization event,
   characterized in that, in step a), at least one oligonucleotide 1 labeled with a label 1, which is completely or partly complementary to the target sequence, functions as a primer in the matrix-dependent de novo synthesis of the target nucleic acid and, in step b), at least one oligonucleotide 2 labeled with a label 2, which by virtue of the lower melting temperature than that of oligonucleotide 1 does not participate in step a), but hybridizes partly or completely with the DNA de novo synthesis product of oligonucleotide 1.

2. A method according to Embodiment 1, characterized in that that the detection of the detection of the hybridization event takes place in the reaction cavity, in which the actual matrix-dependent DNA de novo synthesis of the target nucleic acid and the hybridization reaction are also occurring.

3. A method according to Embodiment 1, characterized in that the detection of the detection of the hybridization event takes place inside or outside the reaction cavity on a solid phase, preferably by means of a test based on a lateral-flow strip.

4. A method according to Embodiment 2, characterized in that the two labels 1 and 2 function as a FRET pair, preferably in the form of FITC/TAMRA, FAM/TAMRA or FAM/BHQ1, and the detection of the fluorescence reduction taking place as a result of a FRET effect leads in form of a measurable decrease of the fluorescence.

5. A method according to Embodiment 4, characterized in that detection as a result of the FRET effect takes place by means of end-point detection.

6. A method according to Embodiment 1, characterized in that, after step a), the reaction batch is heated to a temperature of >90° C., whereupon thermal strand separation takes place, and thereafter the reaction batch is cooled to the hybridization temperature of oligonucleotide 2.

7. A method according to one of Embodiments 1 to 6, characterized in that the hybridized oligonucleotide 2 is not destroyed by the Taq polymerase during the DNA de novo synthesis/hybridization, but instead remains in the hybridized state even after the end of the reaction.

8. A method according to one of Embodiments 1 to 7, characterized in that the detection of the hybridization event takes place only after the conclusion of the DNA de novo synthesis/hybridization.

9. A method according to Embodiment 3, characterized in that the solid phase contains a binding site for one of the labels of oligonucleotide 1 or oligonucleotide 2 and/or antibodies or other binding molecules against the labeling molecules of oligonucleotide 1 or oligonucleotide 2 that bind to the labeling molecules of oligonucleotide 1 or oligonucleotide 2 and at the same time contains at least one detection molecule for visualization or measurement of the hybridization event.

10. A method according to one of Embodiments 1 to 9, characterized in that oligonucleotide 2 is protected against the 5' 4 3'-polymerase activity, preferably by the label itself or by phosphorylation.

11. A test kit for performing the method according to one of Embodiments 1 to 10, comprising:
  at least one oligonucleotide, which is labeled by a label 1, is completely or partly complementary to the target sequence and functions as a primer in a matrix-dependent de novo synthesis of the target nucleic acid (oligo type 1)
  at least one oligonucleotide labeled with a label 2, which by virtue of the lower melting temperature than that of oligonucleotide 1 does not participate in the DNA de novo synthesis process, but is able to hybridize partly or completely with the DNA de novo synthesis product of oligo type 1 (oligo type 2)
  a mixture of chemicals/enzymes, possibly also with further unlabeled oligonucleotides, for permitting a matrix-dependent de novo synthesis of the target nucleic acid.

12. A test kit according to Embodiment 11, characterized in that the melting temperature ($T_m$) of oligonucleotide 2 is 5° C. to 15° C. lower than that of oligonucleotide 1.

BRIEF DESCRIPTION OF DRAWINGS

FIG. 2 shows a fluorescence measurement after the end of the amplification/hybridization reaction.

FIG. 4 shows another fluorescence measurement after the end of the amplification/hybridization reaction.

DETAILED DESCRIPTION OF THE INVENTION

Figure 1:
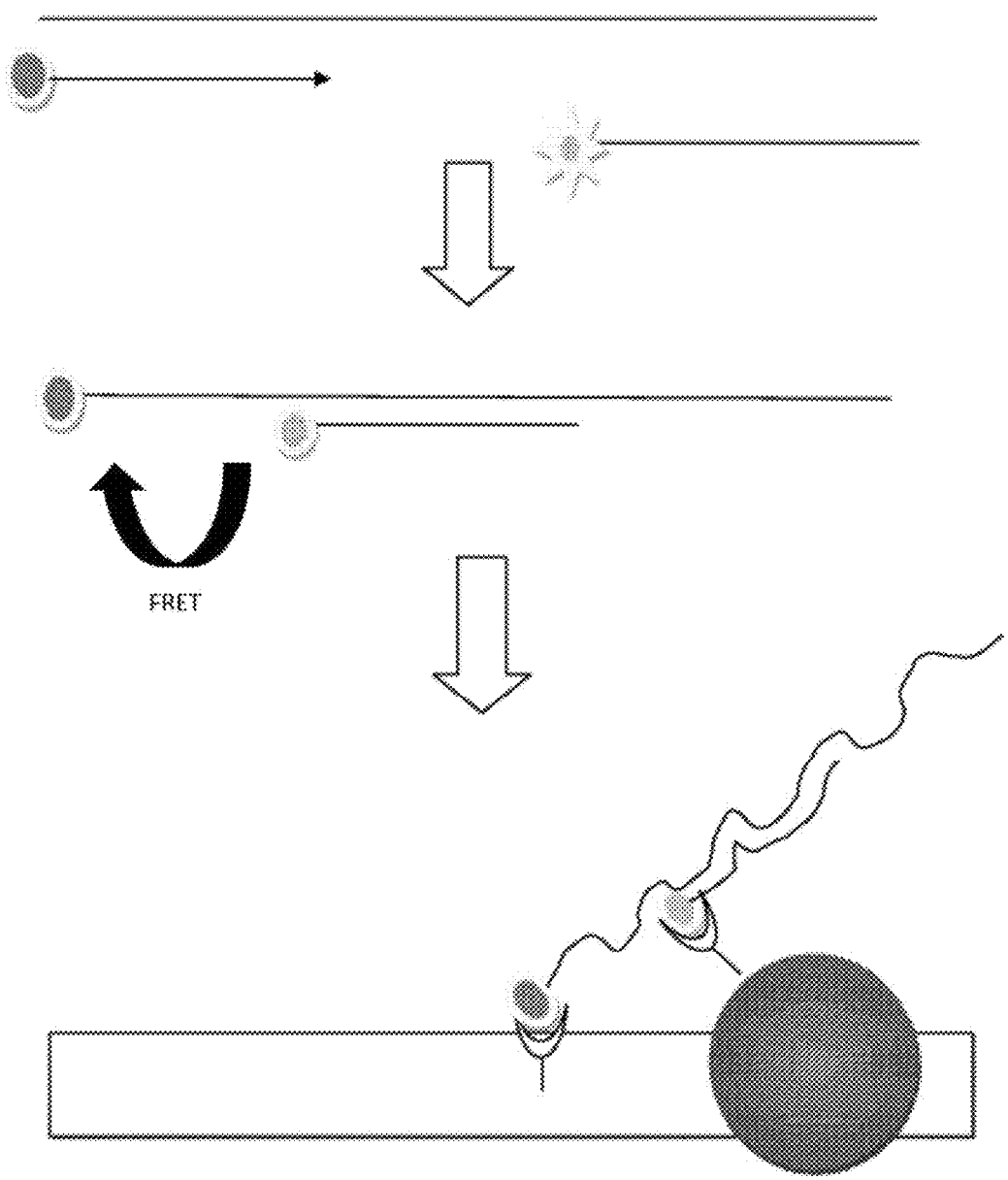
FIG. 1 shows a diagram of the process flow.

Any ranges mentioned herein below include all values and subvalues between the lowest and highest limit of this range.

This inventive method is based on the following steps:
A. Supplying a Reaction Batch, Consisting of:
  a sample containing a nucleic acid, in which the target nucleic acid is to be detected
  at least one oligonucleotide labeled with a label 1, which is completely or partly complementary to the target sequence and functions as a primer in a matrix-dependent de novo synthesis of the target nucleic acid (oligo type 1)
  at least one oligonucleotide labeled with a label 2, which by virtue of the lower melting temperature than that of oligonucleotide 1 does not participate in the DNA de novo synthesis process, but is able to hybridize partly or completely with the DNA de novo synthesis product of oligonucleotide 1 (oligo type 2)
  a mixture of chemicals/enzymes, possibly also with further unlabeled oligonucleotides, for permitting a matrix-dependent de novo synthesis of the target nucleic acid.

As used in the invention, the term "partly complementary" means that sufficient complementarity must be present. In the present case, at least 50%, preferably 70% of the labeled oligonucleotide must be complementary to the target nucleic acid.

As used in the invention, the term "matrix-dependent" means that the de novo synthesis of the target nucleic acid is controlled by the primers being used.

According to the invention, the labels of the two oligonucleotides (oligo type 1 and oligo type 2) are chosen such that together they form a FRET pair (such as FITC/TAMRA, FAM/TAMRA, FAM/BHQ1, etc.) and, in relation to the inventive dual detection, are also capable of having complementary binding partners on a lateral-flow strip.

B. Performing the Matrix-Dependent DNA De Novo Synthesis with Integrated Probe Hybridization Depending on the type of target nucleic acid, there is performed either a reverse transcriptase reaction (in the case of RNA, which occurs in a very large number of copies, such as rRNA, tmRNA) or amplification (in the case of DNA); it is even possible (in the case of a rare RNA, such as mRNA, samples with a small number of particles) to perform the two reactions in succession.

By virtue of the inventive method, only oligo type 1 participates in this first reaction. The oligo type 1 functions as a primer either in an RNA-dependent reverse transcription (whereby a labeled cDNA strand is formed) or in amplification of the target DNA or cDNA (whereby a labeled PCR product is formed). One-step RT-PCR can also be performed. In this process a second unlabeled primer oligonucleotide increases the yield of the PCR reaction.

By virtue of its lower annealing temperature in accordance with the inventive method, the oligo type 2 does not participate in the DNA de novo synthesis. Thereafter the reaction batch is heated to a temperature of >90° C. This step leads to thermal separation of the strands. After the end of this thermal denaturing reaction, the reaction batch is cooled to the hybridization temperature of the oligo type 2. During this step, the oligo type 2 binds specifically to the complementary DNA strand. This strand then carries label 1, which was incorporated into the reaction product by the oligo type 1.

C. Detection of the Hybridization Event

The detection reaction can take place in two variants, but according to the invention the two detection variants may also be used in parallel or else may even be combined as a verification reaction.

1. Detection of the Hybridization Reaction by Means of a Fluorescence Measurement.

The labels incorporated by the two oligos type 1 and type 2 form a FRET pair. The hybridization of the oligo type 2 with the synthesis product of the oligo type 1 that takes place in the inventive method leads to a FRET effect between labels 1 and 2. This effect now leads to a measurable decrease of the fluorescence. This reduction of the fluorescence is numerically evaluated, thus permitting unambiguous detection of the reaction.

2. Detection of the Hybridization Reaction Outside or Inside the Reaction Vessel on a Solid Phase, Characterized in that:

The solid phase (e.g. a lateral-flow strip, microtiter plate, microparticle) contains a binding site for one of the labels of oligo type 1 or type 2 and/or antibodies or other binding molecules against the labeling molecules of oligos type 1 or type 2 that are able to bind to the labeling molecules of type 1 or type 2 (for example, covalent bonds or hydrogen bonds or via bridging molecules). Furthermore, a detection molecule for visualization or measurement of the hybridization event is located on the solid phase, or such a detection molecule is added to the detection reaction. However, it is also possible to incorporate the detection molecule into the hybridization product to be detected as early as during the amplification/hybridization reaction.

In summary, an extremely simple and universally usable detection method for gene diagnostics is now available with the inventive method.

According to the invention, the detection of a diagnostically relevant target nucleic acid to be detected takes place in the form of a homogeneous assay via the end-point fluorescence measurement of fluorescence quenching. The result can be acquired numerically and it also permits quantification of the target nucleic acid to be detected (using an internal standard) detected and quantified. Furthermore, the inventive method also permits highly specific dual detection, since after fluorescence detection has been achieved the result can be verified on a lateral-flow strip. From the diagnostic viewpoint, such a verification is therefore very much more exact than the detection that has been possible heretofore of real-time PCR products on an agarose gel. If necessary, the method also makes it possible to perform the tests independently of one another (test by means of fluorescence detection or test by means of detection on, for example, a lateral-flow strip).

This elegant novel test procedure, and especially also the combined test procedure (fluorescence detection followed by verification of the first test reaction on a solid phase), are made possible according to the invention by the fact that the hybridized probe (oligo type 2) is not decomposed by the Taq polymerase during amplification/hybridization but instead remains in the hybridized condition even after the end of the reaction, in contrast to the homogeneous TaqMan exonuclease assay.

The inventive integration of a hybridization probe into the reaction provides the certainty that the amplified fragment actually contains the target sequence. Thereby false-positive results caused by mispriming are excluded. The use of the chemically modified probe (preferably phosphorylation of the last nucleotide of the probe) prevents the extension of the probe by 5'→3' polymerase activity and thus prevents the probe from functioning as a primer and generating unspecific PCR artifacts (primer dimers), which would be detected as false-positive signals.

In contrast to real-time PCR methods, the detection of the specific detection signal takes place not during amplification, where the fluorescence is released either due to the probe hydrolysis caused by the Taq polymerase (EP 0972848 A2) or is reduced by the FRET effect (EP 1384789 B1), but only after the end of the amplification-hybridization reaction. This also causes the positive effect that the method is independent of instrumental equipment. Measurements may be made both in a real-time PCR instrument and after the end of the reaction with a fluorescence reader (see exemplary embodiments).

The inventive method also differs from the patent (EP 0826066 B1) that also describes a combination of PCR and hybridization. In this method also, a FRET-effect-mediated fluorescence signal is again detected. This occurs during the process of amplification by hybridization of a doubly labeled probe having a lower annealing temperature than that of the primer. The release of fluorescence in this case takes place not by hydrolysis of the probe as a result of the exonuclease activity of the polymerase but instead by the fact that the secondary structure of the probe is loosened during hybridization and fluorescence is released by the increase of the distance of the reporter from the quencher. In this case only enzymes having no exonuclease activity (e.g. Klenow fragments or T4 or T7 polymerases) can be used for amplification.

For the first time there has been achieved a homogeneous method for detecting the presence of a target nucleic acid in a sample, wherein the reaction batch contains:
  a sample nucleic acid, in which the target nucleic acid is suspected
  at least one oligonucleotide, which is labeled by a label 1, is completely or partly complementary to the target sequence and functions as a primer in a matrix-dependent de novo synthesis of the target nucleic acid (oligo type 1)
  at least one oligonucleotide labeled with a label 2, which by virtue of the lower melting temperature than that of oligonucleotide 1 does not participate in the DNA de novo synthesis process, but is able to hybridize partly or completely with the DNA de novo synthesis product of oligo type 1 (oligo type 2)
  a mixture of chemicals/enzymes, possibly also with further unlabeled oligonucleotides, for permitting a matrix-dependent de novo synthesis of the target nucleic acid.

The method comprises the following steps:
  matrix-dependent de novo synthesis of the target nucleic acid to be detected with at least one oligo of type 1 and possibly subsequent strand separation
  hybridization of the synthesis product of the respective oligo type 1 with at least one oligo type 2
  detection of the hybridization reaction by means of a fluorescence measurement.

Labels 1 and 2 form a FRET pair. The hybridization of the oligo type 2 with the synthesis product of the oligo type 1 leads to a measurable decrease of the fluorescence caused by the FRET effect between labels 1 and 2.

Detection of the hybridization reaction is possible outside or inside the reaction vessel. In the case of detection on a solid phase, the solid phase contains a binding site for one of the labels of the oligo type 1 or type 2 and/or antibodies or other binding molecules against the labeling molecules of oligos type 1 or type 2, which bind to the labeling molecules of type 1 or type 2 (for example, covalent bonds or hydrogen bonds or via bridging molecules) and at the same time a detection molecule for visualization or measurement of the hybridization event, or such a molecule is added to the sample bound to the solid phase.

Oligos type 1 and type 2 may also carry labels other than the labels named in Embodiment 4. The additional labels may be used for detection of the hybridization event on the solid phase (1e).

It is also possible to perform an asymmetric amplification instead of the standard amplification.

According to a preferred embodiment of the invention, the melting temperature ($T_m$) of oligo type 1 is preferably 5° C. to 15° C. higher than the $T_m$ of oligo type 2. After hybridization, labels 1 and 2 are preferably 1 to 50 bp apart from one another.

It is also possible for the oligo with a reporter label to be present in the reaction in a lower concentration than the oligo with the quencher label, preferably in the ratio of 1:10 to 1:20.

The inventive method will be described hereinafter on the basis of exemplary embodiments, but the exemplary embodiments are not to be construed as any limitation of the method.

EXAMPLES

Example 1

Detection of Influenza Type H1N1 (swine origin cDNA) by means of hybridization methods integrated into the PCR and end-point fluorescence measurement of fluorescence quenching Negative samples (NTC), H1N1 cDNA-positive samples (POS) and the samples that indeed contained human DNA material (swab smear of nasal mucous membranes) but not H1N1 (NEG) were present in the batch.

The possibility of an inventive end-point fluorescence measurement and the specificity of the method will be demonstrated with this example.

PCR Primer/Probe

H1N1 sense primer
(SEQ ID NO: 1)
(5'-tgg gaa atc cag agt gtg aat cac tct c-3')

H1N1 antisense primer (oligo type 1)
(SEQ ID NO: 2)
(5'-BHQ1-cgt tcc att gtc tga act agr tgt ttc c-3')

H1N1 probe (oligo type 2)
(SEQ ID NO: 3)
(5'-agc aag ctc atg gtc cta cat t-FAM-3')

Samples: 3×POS; 3×NEG; 3×NTC
Per sample:

| | |
|---|---|
| sense primer (25 pmol/μL) | 0.1 μL |
| antisense primer (50 pmol/μL) | 0.1 μL |
| probe (5 pmol/μL) | 0.1 μL |
| dNTP mix (12.5 mM) | 0.3 μL |
| 10X PCR buffer (MgCl$_2$ included) | 1.5 μL |
| Taq-DNA polymerase | 0.75 U |
| PCR grade H$_2$O | add 15 μL |

The PCR was carried out in the SpeedCycler (Analytik Jena) using the rapid cycler technology:
Amplification/Hybridization Conditions

| | |
|---|---|
| Step 1: denaturing | 98° C./90 sec |
| Step 2: amplification for 41 cycles (98° C./4 sec; 57° C./4 sec; 72° C./10 sec) | |
| Step 3: denaturing | 95° C./900 sec |
| Step 4: hybridization: | 43° C./600 sec |

Figure 3:
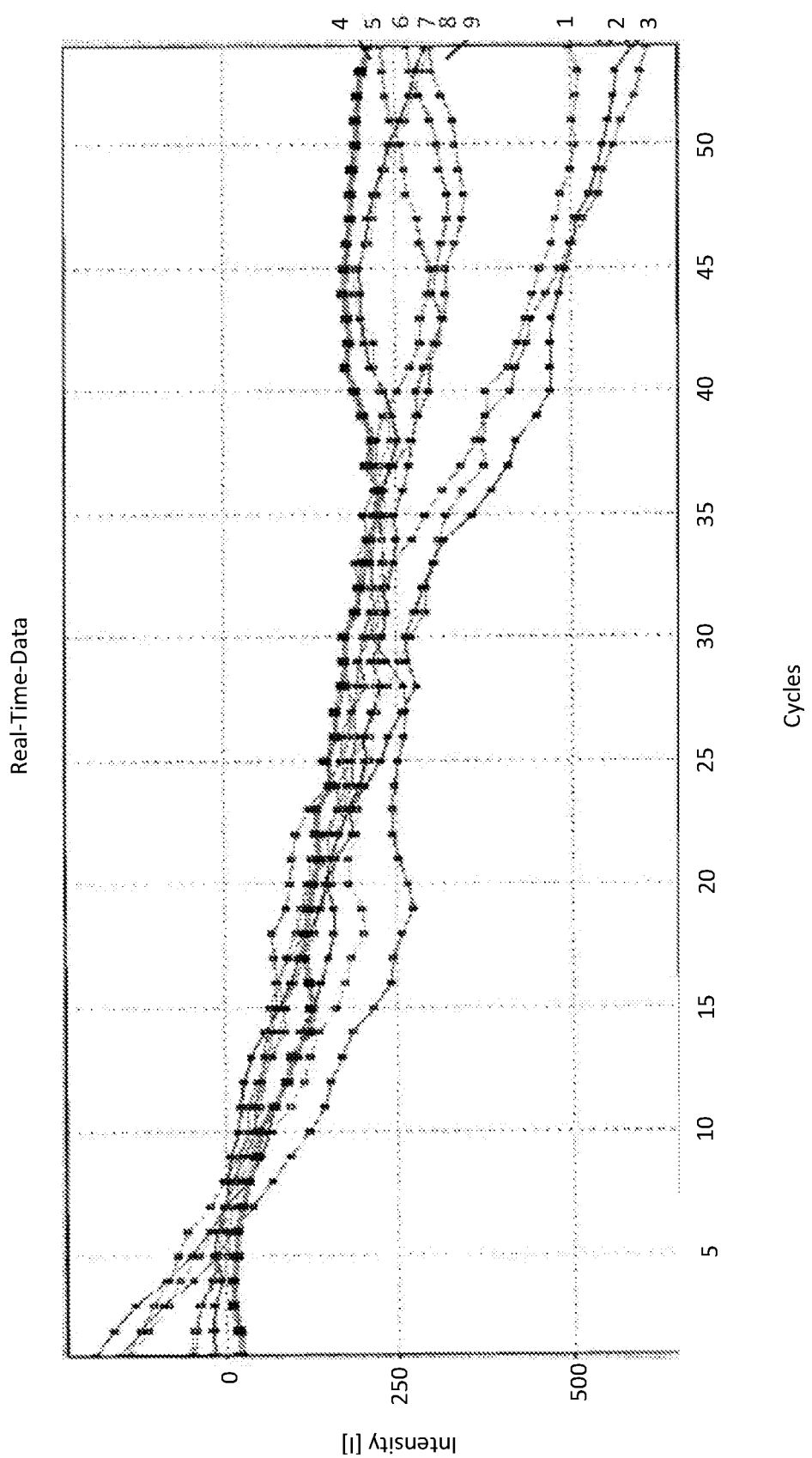
FIG. 3 shows a real-time fluorescence measurement during the entire amplification/hybridization reaction.

The amplification event/the hybridization reaction was detected by means of an end-point measurement with the SpeedScan fluorescence reader (Analytik Jena AG; FIG. 2). At the same time, the change of fluorescence intensity of the sample was measured in real time during the entire reaction (FIG. 3). The measured data of the SpeedScan instrument were subjected to a Pos/Neg determination according to the following formula:

$$\overline{x}N - xN_{min} + \% \overline{x}N = A$$

$$\overline{x}N - P = B$$

if $A - B \geq 0$, the sample is negative if $A - B < 0$, the sample is positive Where $\overline{x}N$ is the mean value of the NTC values; $xN_{min}$ is the smallest NTC value; desired percentage deviation of the positive value from the negative value (e.g. 20% of $\overline{x}N$), and P is the measured value of the sample to be tested.

Furthermore, the sample may be evaluated semi-quantitatively by using a concentration standard.

Nevertheless, a truly quantitative evaluation is possible only in the presence of an internal control and a competitive reaction.

The results of the qualitative evaluation of the sample fluorescence are summarized in Table 1.

| Sample ID | Measured value after the PCR | Value A at 20% | Value B | A − B | pos/neg |
|---|---|---|---|---|---|
| Pos | 3447 | 11485 | 15506 | −4021 | POS |
| Pos | 6533 | 11485 | 12420 | −935 | POS |
| Pos | 6024 | 11485 | 12929 | −1444 | POS |
| Neg | 18408 | 11485 | 5573 | 5912 | NEG |
| Neg | 11764 | 11485 | 7189 | 4296 | NEG |
| Neg | 18937 | 11485 | 16 | 11469 | NEG |
| NTC | 11258 | 11485 | 7695 | 3790 | NEG |
| NTC | 26666 | 11485 | −7713 | 19198 | NEG |
| NTC | 18937 | 11485 | 16 | 11469 | NEG |

Example 2

Dependence of Signal Intensity on the Concentration of the Target DNA in Comparison with a Conventional Real-Time PCR Two batches were prepared: for the inventive method and a real-time PCR batch with a probe labeled with FAM-BHQ1. The cDNAs (see table for particle count/PCR batch) synthesized from Influenza H1N1 virus strains were used as samples.

Batch 1: See Example 1 for the reaction conditions
Batch 2:
PCR Primer/Probe
H1N1 RT sense primer (5'-tgg gaa atc cag agt gtg aat cac t-c-3') (SEQ ID NO:4)
H1N1 RT antisense primer (5'-cgt tcc att gtc tga act agr tgt t-3') (SEQ ID NO:5)
H1N1 RT probe (5'-FAM-cca caa tgt agg acc atg agc ttg ctg t-BHQ1-3') (SEQ ID NO:6)
Per sample:

| | |
|---|---|
| sense primer (50 pmol/μL) | 0.1 μL |
| antisense primer (50 pmol/μL) | 0.1 μL |
| probe (25 pmol/μL) | 0.1 μL |
| dNTP mix (12.5 mM) | 0.3 μL |
| 10X PCR buffer (MgCl$_2$ included) | 1.5 μL |
| Taq-DNA polymerase | 0.75 U |
| PCR grade H$_2$O | add 15 μL |

The PCR was carried out in the SpeedCycler (Analytik Jena) using the rapid cycler technology:

Amplification/Hybridization Conditions

| Step 1: denaturing | 98° C./90 sec |
|---|---|
| Step 2: amplification | 41 cycles (98° C./4 sec; 57° C./4 sec; 72° C./10 sec) |

Figure 5:
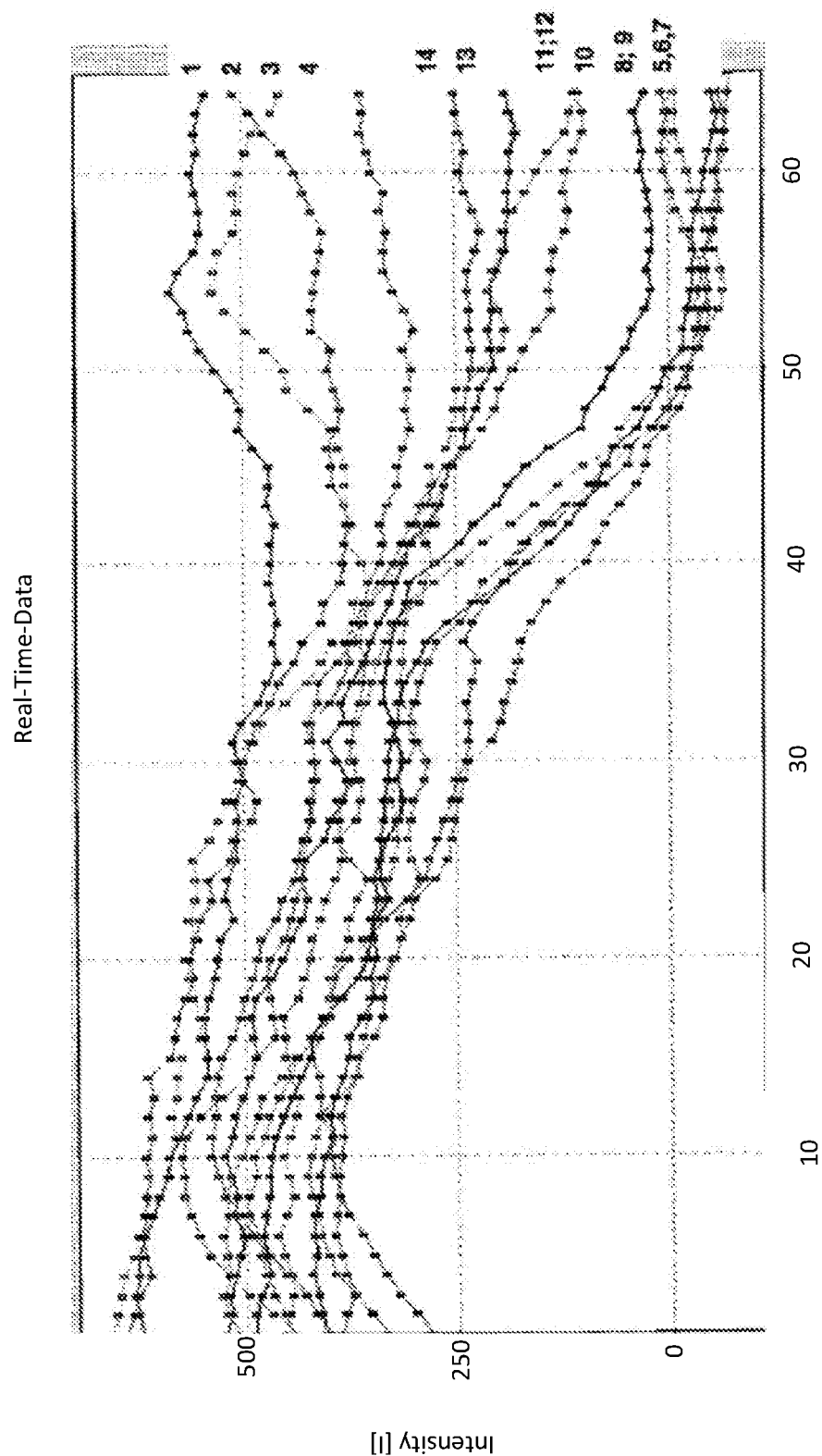
FIG. 5 shows another real-time fluorescence measurement during the entire amplification/hybridization reaction.

The amplification event/the hybridization reaction in Batch 1 was detected by means of an end-point measurement of the fluorescence by means of SpeedScan (Analytik Jena AG; FIG. 4). At the same time, the change of fluorescence intensity of the sample was observed in real time (real-time PCR) during the entire reaction (FIG. 5). The measured data of the SpeedScan instrument were subjected to a Pos/Neg determination according to the formula described hereinabove (see Example 1). In Batch 2, the fluorescence release was measured conventionally by means of real-time PCR.

The results of the qualitative evaluation of the sample fluorescence are summarized in Table 2.

| Particle count in the sample | Measured value after the PCR (mean value) | Value A at 20% | Value B | A − B | pos/neg | Ct value of Batch 2 |
|---|---|---|---|---|---|---|
| 10000 | 7547 | 4910 | 7292 | −2382 | POS | 26 |
| 5000 | 3650 | 4910 | 11189 | −6279 | POS | 26 |
| 500 | 9400 | 4910 | 5439 | −529 | POS | 33 |
| 50 | 10816 | 4910 | 4023 | 887 | NEG | 38 |
| 5 | 10590 | 4910 | 4249 | 661 | NEG | NoCt |
| NTC | 14839 | 4910 | 0 | 4910 | NEG | NoCt |

EXPLANATION OF THE FIGURES

FIG. 1 shows a diagram of the process flow.
FIG. 2 shows a fluorescence measurement after the end of the amplification/hybridization reaction. Fields B3-B5 are POS samples, B6-B8 are NEG samples, B9-B11 are NTC samples (measurement of the fluorescence by means of SpeedScan (Analytik Jena AG)).

FIG. 3 shows a real-time fluorescence measurement during the entire amplification/hybridization reaction. Curves 1-3 are POS samples, 4-6 are NEG samples, 7-9 are NTC samples (real-time measurement for tracking of the detection reaction).

FIG. 4 shows a fluorescence measurement after the end of the amplification/hybridization reaction. Fields B3/C3 are POS samples with a virus particle count of 10000; B4/C4 are POS samples with a virus particle count of 5000; B5/C5 are POS samples with a virus particle count of 500; B6/C6 are POS samples with a virus particle count of 50; B74/C7 are POS samples with a virus particle count of 5; B9-B10/C9-C10 are NTC samples.

FIG. 5 shows a real-time fluorescence measurement during the entire amplification/hybridization reaction. Curves 1-4 are NTC samples; samples 5-14 are concentrated as follows: 5, 6-100000 particles/sample; 7, 8-5000 particles/sample; 9, 10-500 particles/sample; sample 11, 12-50 particles/sample; sample 13, 14-5 particles/sample.

Figure 6:
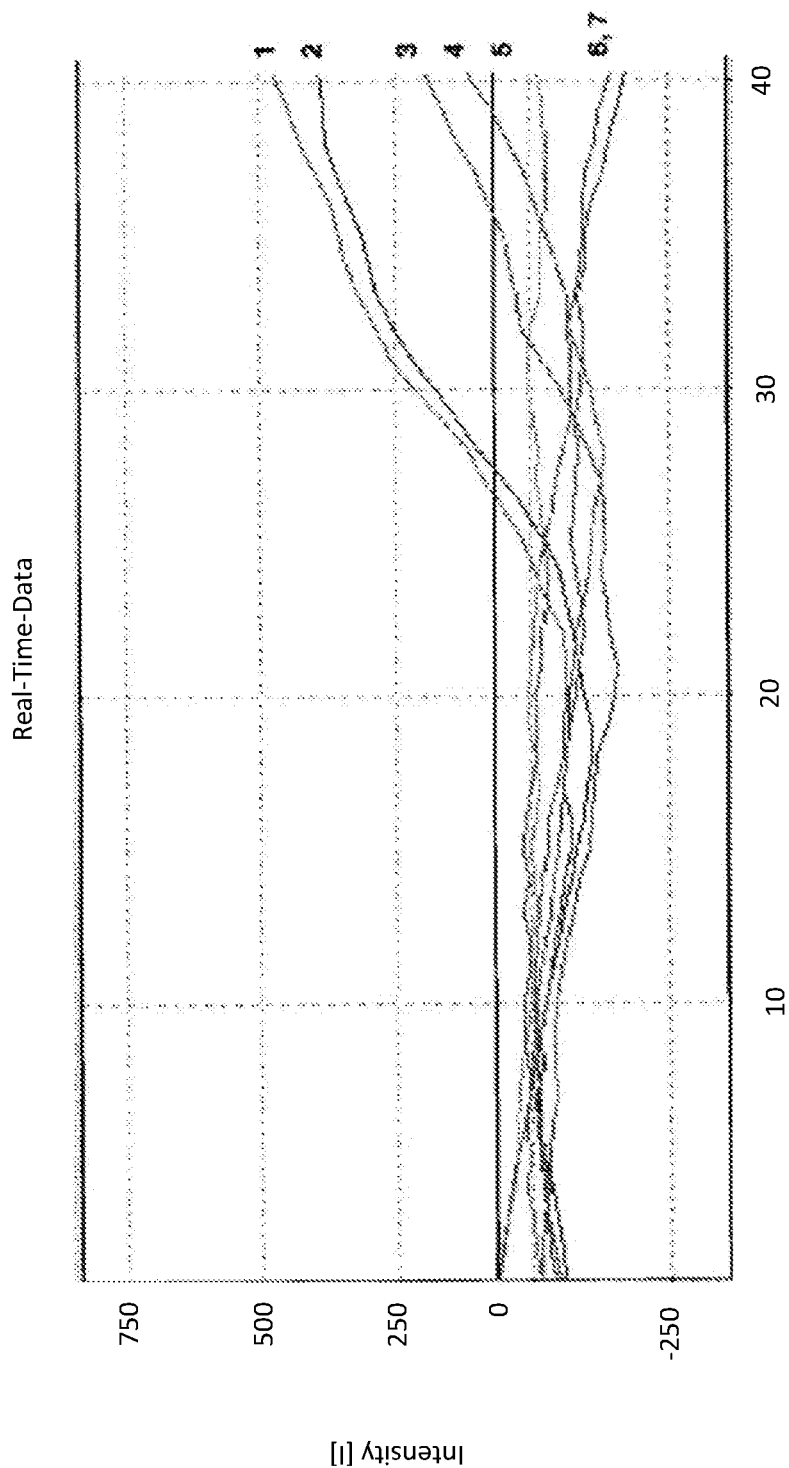
FIG. 6 shows a real-time fluorescence measurement during a real-time reaction with a conventional TaqMan probe.

FIG. 6 shows a real-time fluorescence measurement during a real-time reaction with a conventional TaqMan probe. Curves 6, 7 are NTC samples; samples 1-5 are concentrated as follows: 1-100000 particles/sample; 2-5000 particles/sample; 3-500 particles/sample; sample 4-50 particles/sample; sample 5-5 particles/sample.

Numerous modifications and variations on the present invention are possible in light of the above teachings. It is therefore to be understood that within the scope of the appended claims, the invention may be practiced otherwise than as specifically described herein.

The invention claimed is:

1. A method for detecting a specific nucleic acid sequence, the method comprising:
   a) in a reaction cavity, synthesizing a DNA target nucleic acid comprising a specific nucleic acid sequence in a matrix-dependent de novo manner with a primer and in the presence of a probe and a template of the DNA target nucleic acid, wherein the primer comprises an oligonucleotide 1 labeled with a label 1, the oligonucleotide 1 is completely complementary to the template of the DNA target nucleic acid, wherein the probe hybridizes completely to the DNA target nucleic acid but does not participate in synthesizing the DNA target nucleic acid, wherein the probe comprises an oligonucleotide 2 labeled with a label 2, which has a lower melting temperature than oligonucleotide 1, wherein the oligonucleotide 2 is protected against a 5'→3'-exonuclease activity by phosphorylation of a 3' OH group of the oligonucleotide 2, wherein the label 1 and the label 2 are a fluorescence resonance energy transfer (FRET) pair having a FRET effect, and wherein the probe hybridizes to a location on the DNA target nucleic acid which is synthesized by the primer such that the label 1 of the DNA target nucleic acid and the label 2 of the probe are capable of having FRET effect,
   b) detecting, in the reaction cavity, that the probe hybridizes to the location on the DNA target nucleic acid by measuring a decrease in a fluorescence from the label 1 or the label 2 in a real time, thereby detecting the specific nucleic acid sequence.

2. The method of claim 1, wherein the oligonucleotide 1 or the oligonucleotide 2 is immobilized to a solid phase, and wherein step b) is performed on the solid phase inside of the reaction cavity in which steps a) and b) are performed.

3. The method of claim 1, step a) further comprising, heating a reaction batch comprising the target nucleic acid, the primer, and the probe in the reaction cavity to a temperature of greater than 90° C., and thereafter cooling the reaction batch to a temperature such that the oligonucleotide 2 is hybridized with the DNA target nucleic acid.

4. The method of claim 1, wherein the DNA target nucleic acid is synthesized using a Taq DNA polymerase in step a) and the oligonucleotide 2 is not destroyed by a 5'→3'-exonuclease activity of the Taq DNA polymerase during step a), but instead remains in the reaction cavity after step a).

5. The method of claim 1, wherein step b) is performed only after step a) is finished.

6. The method of claim 1, wherein the FRET pair is selected from the group consisting of:
   fluorescein isothiocyanate/tetramethyl-6-carboxyrhodamine (FITC/TAMRA),
   fluorescein amidite/TAMRA (FAM/TAMRA), and
   FAM/black hole quencher-1 (FAM/BHQ1).

7. The method of claim 1, wherein the melting temperature of the oligonucleotide 2 is 5° C. to 15° C. lower than the melting temperature of the oligonucleotide 1.

8. A method for detecting a specific nucleic acid sequence, the method comprising:
   a) in a reaction cavity, synthesizing a DNA target nucleic acid comprising a specific nucleic acid sequence in a matrix-dependent de novo manner with a primer and in the presence of a probe and a template of the DNA target nucleic acid, wherein the primer comprises an oligonucleotide 1 labeled with a label 1, the oligonucleotide 1 is completely complementary to the template of the DNA target nucleic acid, wherein the probe hybridizes completely to the DNA target nucleic acid but does not participate in synthesizing the DNA target nucleic acid, wherein the probe comprises an oligonucleotide 2 labeled with a label 2, which has a lower melting temperature than oligonucleotide 1 by 5° C. to 15° C., wherein the oligonucleotide 2 is protected against a 5'→3'-exonuclease activity by phosphorylation of a 3' OH group of the oligonucleotide 2, wherein the label 1 and the label 2 are a fluorescence resonance energy transfer (FRET) pair having a FRET effect, and wherein the probe hybridizes to a location on the DNA target nucleic acid which is synthesized by the primer such that the label 1 of the DNA target nucleic acid and label 2 of the probe are capable of having the FRET effect, and b) detecting, in the reaction cavity, that the probe hybridizes to the location on the DNA target nucleic acid by measuring a decrease in a fluorescence from the label 1 or the label 2 in a real time, thereby detecting the specific nucleic acid sequence.

9. The method of claim 1, wherein the FRET pair is FAM/black hole quencher-1 (FAM/BHQ1).

\* \* \* \* \*

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: H1N1 sense Primer

<400> SEQUENCE: 1
tgggaaatcc agagtgtgaa tcactctc                                        28

<210> SEQ ID NO 2
<211> LENGTH: 28
<212> TYPE: DNA
<213> ORGANISM: Artificial Sequence
<220> FEATURE:
<223> OTHER INFORMATION: H1N1 antisense Primer

<400> SEQUENCE: 2
cgttccattg tctgaactag rtgtttcc                                        28

<210> SEQ ID NO 3
<211> LENGTH: 22
<212> TYPE: DNA
<213> ORGANISM: Artificial Sequence
<220> FEATURE:
<223> OTHER INFORMATION: H1N1 probe
```

```
<400> SEQUENCE: 3
agcaagctca tggtcctaca tt                                                22

<210> SEQ ID NO 4
<211> LENGTH: 26
<212> TYPE: DNA
<213> ORGANISM: Artificial Sequence
<220> FEATURE:
<223> OTHER INFORMATION: H1N1 RT sense Primer

<400> SEQUENCE: 4
tgggaaatcc agagtgtgaa tcactc                                            26

<210> SEQ ID NO 5
<211> LENGTH: 25
<212> TYPE: DNA
<213> ORGANISM: Artificial Sequence
<220> FEATURE:
<223> OTHER INFORMATION: H1N1 RT antisense Primer

<400> SEQUENCE: 5
cgttccattg tctgaactag rtgtt                                             25

<210> SEQ ID NO 6
<211> LENGTH: 28
<212> TYPE: DNA
<213> ORGANISM: Artificial Sequence
<220> FEATURE:
<223> OTHER INFORMATION: H1N1 RT probe

<400> SEQUENCE: 6
ccacaatgta ggaccatgag cttgctgt                                          28
```